United States Patent [19]

Wallach

[11] 4,239,780
[45] Dec. 16, 1980

[54] PHOSPHOLIPASE A₂ INHIBITION

[75] Inventor: Donald P. Wallach, Richland, Mich.

[73] Assignee: The Upjohn Company, Kalamazoo, Mich.

[21] Appl. No.: 84,022

[22] Filed: Oct. 11, 1979

[51] Int. Cl.³ .......................................... A61K 31/135
[52] U.S. Cl. .................................................... 424/330
[58] Field of Search ....................................... 424/330

[56] References Cited

U.S. PATENT DOCUMENTS 3,979,444  9/1976  Lednicer .......................... 424/248.52

*Primary Examiner*—Stanley J. Friedman
*Attorney, Agent, or Firm*—Lawrence T. Welch

[57] ABSTRACT

Phospholipase A₂ inhibition the present invention relates to a method for treating or preventing a phospholipase A₂ mediated condition (PMC) in a mammal suffering from or susceptible to such a condition. The method involves administering to such a mammal an amount effective to treat the condition of a compound selected from a certain group of butyrophenones.

1 Claim, No Drawings

PHOSPHOLIPASE A₂ INHIBITION

BACKGROUND OF THE INVENTION

The present invention relates to novel methods of using known pharmacological agents. These novel methods are to be used in the treatment of conditions or symptoms due to certain disease conditions in mammals. In particular this invention relates to a novel method of inhibiting the formation of products of the "arachidonic acid cascade" in such pathological states. This inhibition is accomplished by inhibiting the action of the enzyme phospholipase $A_2$, an important mediator in the cascade, by administering certain butyrophenones.

The important role of phospholipase $A_2$ in mammalian metabolism through the formation of prostaglandins is now well known. See W. Vogt, Advances in Prostaglandin and Thromboxane Research, Vol. 3, page 89, (1978); P. C. Isakson, et al., Advances in Prostaglandin and Thromboxane Research, Vol. 3, page 113, (1978). Phospholipase $A_2$ is responsible for the hydrolysis of arachidonic acid-containing phospholipids, thereby providing substrate for the multiple enzymes of the arachidonic acid cascade.

The products of the arachidonic acid cascade are varied. While generally the products of the cascade are beneficial, in certain disease processes and other conditions the production of prostaglandins and similar products induces deleterious consequences such as inflammation (see paper by N. A. Plummer et al., abstracted in Journal of Investigative Dermatology, Vol. 68, No. 4, p. 246 (1977)); erythema (N. A. Plummer, supra); platelet aggregation (B. B. Vargaftig, J. Pharm. Pharmacol., Vol. 29, p. 222–228 (1977)); and the release of SRS-A (slow reacting substance-anaphylaxis), a known mediator of allergenic responses. The inhibition of phospholipase $A_2$ prevents these and similar conditions mediated by the action of this enzyme.

The butyrophenones of this invention are known hypotensive agents. They are prepared by conventional means. These compounds have been found surprisingly and unexpectedly to inhibit phospholipase $A_2$.

Prior Art

Some inhibitors of phospholipase $A_2$ are known. Anti-inflammatory steroids are one example. R. J. Flower and G. J. Blackwell have shown that these steroids induce biosynthesis of a phospholipase $A_2$ inhibitor which prevents prostaglandin generation. See Nature, Vol. 278, p. 456, (1979). As such, steroids are not direct inhibitors of phospholipase $A_2$, but rather stimulate the syntheses of a phospholipase inhibiting factor (presumed to be a peptide).

Some examples of direct inhibition are known. Indomethacin, a drug with anti-inflammatory properties, has been shown to inhibit at least one phospholipase $A_2$ enzyme. See L. Kaplin, et al., Proc. Natl. Acad. Sci., Vol. 75, No. 6, pp. 2955–2988 (1978). The compound has been shown to inhibit phospholipase $A_2$ of rabbit polymorphonuclear leukocytes in dose dependent fashion. However, indomethacin has been found inactive in the inhibition of four other phospholipase $A_2$ enzymes, isolated respectively from the venoms of Russel Viper, Crotalus Adamanteus, and bee, and from pig pancreas. Certain local anesthetics have been shown to inhibit phospholipase $A_2$ activity by competing with calcium ion, which appears to be a requirement for phospholipase activity. See W. Vogt, Advances in Prostaglandin and Thromboxane Research, Vol. 3, p. 89 (1978). Bromphenacyl bromide has been shown to inhibit phospholipase $A_2$ by acylating a histadine residue which is the active site of the molecule. See M. Roberts, et al., Journal of Biological Chemistry, Vol. 252, pp. 2405–2411 (1977). R. Blackwell et al., in British Journal of Pharmacy, Vol. 62, p. 79–89 (1978) has disclosed that meparine inhibits the activity of phospholipase $A_2$ derived from perfused guinea pig lung.

The butyrophenones which are disclosed as phospholipase $A_2$ inhibitors in the present invention were previously known as hypotensive agents. (see D. Lednicer et al., Journal of Medicinal Chemistry, Vol. 18, page 593 (1975)). See also U.S. Pat. No. 3,979,444.

SUMMARY OF THE INVENTION

This invention involves the use of some known pharmacological agents to inhibit phospholiphase $A_2$. The compounds have been shown to be inhibitive of phospholipase $A_2$ from a number of sources including: snake venom, bee venom, hog pancrease, and human platelets. They have also been shown to be active inhibitors in vivo in a guinea pig as shown by a reduced erythema, induced by ultraviolet light.

More specifically, the present invention comprises a method for treating or preventing a phospholipase $A_2$ mediated condition (PMC) in a mammal suffering from or susceptible to the development of said PMC which comprises administering to said mammal an amount of a compound of formula I:

$$R_1\text{-N}(R_3)\text{-CH}_2\text{-CH}_2\text{-CH}_2\text{-R}_2$$

wherein $R_1$ is

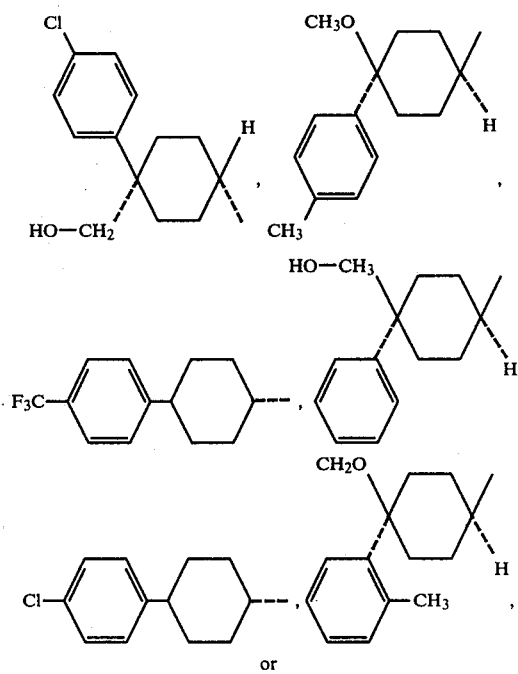

or

-continued

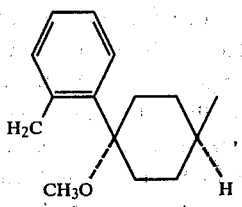

R₂ is

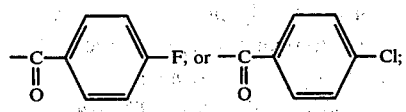

R₃ is H or CH₃, with the proviso that R₃ is -CH₃ only when R₁ is

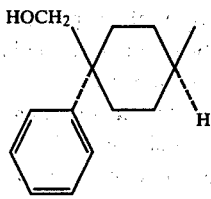

or a pharmacologically acceptable acid addition salt or salt-hydrate thereof, effective to treat or prevent said PMC.

The above compounds of Formula I are known. For example, D. Lednicer et al., in Journal of Medicinal Chemistry, Vol. 18, page 593 (1975), has disclosed that the compounds of this invention, best described as butyrophenones, are known hypotensive agents. They are prepared by conventional methods as disclosed therein. One such method is according to the following scheme of Chart A. A hydroxy acetate of formula IV is converted to its mesylate by means of mesylchloride in pyridine. Treatment of the resulting compound V with sodium azide in DMF followed by reduction of the crude intermediate with lithium aluminum hydride leads to reduction of both the azide and acetate groups. The amino alcohol of the formula VI thus obtained is converted to the butyrophonone by condensation with 2,2-dimethylpropyleneketal of 4'-chloro-(p-fluoro)-butyro phenone, followed by deketalization. Other schemes are disclosed in U.S. Pat. No. 3,979,444.

The compounds of this invention are thus prepared by these means. These known hypotensive agents have surprising and unexpected phospholipase A₂ inhibitory activity, as shown below.

The symptoms or conditions treated or prevented by the method of this invention are those which are produced as a result of the excessive stimulation of the arachidonic acid cascade during certain disease processes or conditions. The multiple enzymes of the cascade act upon unsaturated fatty acids to produce prostaglandins and similar products. At certain times during these disease processes or conditions, some of these products are responsible for the symptoms or conditions noted above, e.g., inflammation, erythema, allergic responses, and similar conditions. Phospholipase A₂ provides the substrate for these enzymes of the cascade by hydrolysis of arachidonate rich phospholipids. Thus, phospholipase A₂ is an important mediator in these conditions. Inhibition of this enzyme by the method of this invention is thus effective to treat or prevent the symptoms or conditions, which are designated as PMC's (phospholipase A₂ mediated conditions).

The precise mechanisms of the disease processes or conditions which stimulate the arachidonic acid cascade are not clearly understood. The method of this invention works by preventing the action of the cascade despite the cascade stimulating conditions. Thus, the method of this invention is suitable for treating seemingly unrelated diseases whose common element is the stimulation of the arachidonic acid cascade. The term "phospholipase A₂ mediated conditions" (PMC) includes all untoward conditions or symptoms which are the result of the excessive stimulation of the arachidonic acid cascade. Some disease processes and conditions which stimulate the cascade include: burns, exposure to allergenic substances, and inflammatory diseases e.g., rhematoid arthritis. The method of this invention is also useful in treating a PMC caused by any other disease process or condition.

The method of this invention could be used on any mammal whose metabolic system includes the phospholipase induced arachidonic acid cascade. The mammals which are preferred are generally domesticated animals and humans. Humans are the most preferred mammals to be treated by the method of this invention.

The method of this invention is useful both in treating a phospholipase A₂ mediated condition (PMC) or symptom which has already manifested itself in the mammal as well as the prevention of these conditions or symptoms in mammals particularly susceptible to them. Employment of the method of this invention prior to the development of a PMC would prevent the formation of the prostaglandins and similar products necessary for such conditions. Thus, the method of this invention can be used to prevent edema and erythema from sunburn by administering these compounds prior to exposure to sunlight. The compounds of this invention could be administered to persons suffering from hayfever or similar allergies prior to exposure to allergenic substances which are particularly hard on hayfever suffers. In a like manner, a physician or veterinarian could readily determine other mammals or persons susceptible to a PMC.

Once a PMC has manifested itself a physician or veternarian could readily determine the necessity of employing the process of this invention.

The actual inhibition of phospholipase A₂ by the method of this invention takes place on a cellular level. Administration of the compound of this invention can thus be by any manner which will allow for phospholipase A₂ inhibition in the affected tissues or organs. The preferred route in most cases would be to systemically administer the compounds, i.e., to allow them to enter the mammal's bloodstream and thus be administered throughout the mammal's system. In certain cases, where the PMC is of a localized nature (e.g., sunburn), topical administration (e.g., transdermal) may be employed in order that the phospholipase A₂ inhibition is confined to the afflicted area.

Since the diseases or conditions formed as a result of the arachidonic acid cascade are varied, methods of administering these compounds must depend on the particular phospholipase mediated condition (PMC) sought to be treated. Regardless of the route of administration selected the compounds used in the process of the present invention are formulated into pharmaceutically acceptable dosage form by conventional methods known to the pharmaceutical art.

Thus, the compounds can be administered orally in forms such as pills, capsules, solutions or suspensions. They may also be administered rectally or vaginally in forms such as suppositories or bougies. They may also be introduced interparenterally, subcutaneously, or intramuscularly using sterile injectable forms known to the pharmaceutical art. For treatment of conditions such as erythema the compounds of this invention may also be administered topically in the form of ointments, gels, or the like.

In general the preferred form of administration is orally.

The dosage regimen for preventing or treating phospholipase mediated conditions (PMC) by the compounds of this invention is selected in accordance with a variety of factors, including the type, age, weight, sex and medical condition of the mammal, the severity of the PMC and the particular compound employed. An ordinarily skilled physician or veterinarian will readily determine and prescribe the effective amount of the anti-PMC agent to prevent or arrest the progress of the condition. In so proceeding the physician or veterinarian could employ relatively low dosages at first, subsequently increasing the dose until a maximium response is obtained.

Initial dosages of the compounds of this invention can be from 0.5 to 2.0 g. per 70 kg. mammal per 8 hrs. orally. When other forms of administration are employed, equivalent doses are administered. When dosages beyond 2.0 g. per 70 kg. mammal per 8 hrs. are employed, care should be taken with each subsequent dose to monitor possible toxic effects.

The compounds of this invention can also be administered as pharmacologically acceptable acid addition salts such as the hydrochloride, hydrobromide, hydroiodide, sulfate, phosphate, acetate, propionate, lactate, maleate, malate, succinate, tartrate, and the like. These salts may also be in hydrated form.

DESCRIPTION OF THE PREFERRED EMBODIMENTS

The compounds used in the method of the present invention are inhibitors of phospholipase $A_2$ as shown by one or more of the following tests.

EXAMPLE 1

The first three tests involve the use of a coupled assay system. In this system the action of the phosphilipase $A_2$ was linked to soybean lipoxygenase. Hydrolysis of a phosphtidyl choline (lecithin) substrate by the phospholipase, which contained an appropriate unsaturated fatty acid, generated a substrate (an unsaturated fatty acid) which would be oxidized by the lipoxygenase. The overall reaction of both enzymes was monitored by measurements of oxygen consumption of the system according to the following scheme.

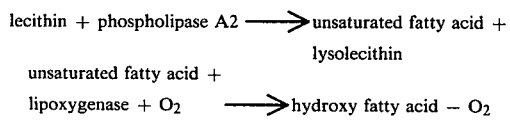

Addition of inhibitors to this system would be immediately detected by diminution or elimination of oxygen consumption. If subsequent addition of arachidonic acid (a substrate for the lipoxygenase) resulted in an oxygen uptake, this was evidence that the phospholipase and not the oxygenase was inhibited. This test was run on compounds of this invention for phospholipases derived from hog pancreas, snake venom, and bee venom. The results are summarized in Tables I, II, and III.

The test was carried out as follows: to a cell containing 2.5 ml. of 0.033 molar ammediol buffer pH 8.5 containing $1 \times 10^{-4}$ molar calcium chloride was added 0.1 ml. of the test compound and 7 to 8 units of the phospholiphase $A_2$. The mixtures were rapidly mixed and incubated for 3 min. at room temperature. At this point 0.05 ml. of a lecithin ammediol buffer suspension was added and mixed as before with the magnetic stirrers in each cell. the oxygraph probes were inserted in the cells, all air was excluded, and the temperature of the contents was raised to 37° C. over a 5 min. incubation period. At this point 0.15 mg. of soybean lipoxidase was added to each cell and oxygen uptake was monitored. After the reaction, addition of arachidonic acid to the reaction mixture resulted in a rapid uptake of oxygen, indicating that the phospholipase and not the lypoxygenase had been inhibited by the test compound. This system was used in two ways, both as a screening technique and as a means of measuring the actual inhibitory activity of the compounds. Thus, for certain compounds a concentration of $3.8 \times 10^{-4}$ molar was used, and if complete inhibition occurred at this concentration the compound was considered "active". In this manner a large number of compounds were screened for possible activity.

To determine the actual activity of compounds a different format was used. Conditions were altered as follows: the test compounds were made up as 0.01 molar solutions in either water or acetone as dictated by the solubility characteristics. Instead of one cell per compound, four cells were used. Where oxygen consumption was nil, the reaction was considered to be 100% inhibited. Lower concentrations of inhibitor were then added to a new set of cells and the reaction was then rerun until partial inhibition was achieved. The slopes of initial rates of the four curves of oxygen consumption, were then determined and the mean and standard deviation were calculated. The percent inhibition was then determined using control samples run under identical conditions but without addition of inhibitor compounds, and the estimated $I_{50}$ was then calculated from a partial inhibition value. The data is tabulated in Tables I, II and III. The ability of these compounds to inhibit phospholipase $A_2$ at low concentrations is apparent.

EXAMPLE 2

The compounds of the present invention were tested for their ability to inhibit collagen-induced aggregation of platelets at 100 μg. per ml. or less. The compounds that were active against collagen-induced aggregation were tested at the $I_{50}$ dose against arachidonic acid-induced aggregation. Compounds that inhibited collagen-induced aggregation, but not arachidonic acid-induced aggregation, were reported as active phospholipase $A_2$ inhibitors.

The test was run as follows. Human blood was drawn from an antecubital vein into 3.8% sodium citrate with the final citrate concentration being 0.38%. The blood was transferred to plastic centrifuge tubes and centrifuged at 200×g for 10 min. This yielded protein rich plasma (PRP). This PRP was allowed to stand for 30 min. for testing at which point it was tested against 400 μg. per ml. of arachidonic acid. If the platelets did not aggregate they were discarded and fresh PRP was made. If the platelets aggregated to arachidonic acid, a dose of collagen that gave a substantial irreversible aggregation (approximately 60-80% transmission) was established. It was then attempted to block the response of collagen with 10 μg. per ml. of indomethacin. If the aggregation was not blocked with indomethacin, too much collagen was being used, and a lower dose of collagen was chosen so that it was completely blocked by 10 μg./ml. of indomethacin. The $ID_{50}$ for all unknown compounds was then established. Most of the compounds were tested at rather high concentrations and it was often necessary to place the compound in ethanol into the aggregation cuvet and evaporate the ethanol before testing.

Compounds that did not inhibit collagen-induced aggregation at 100 μg per ml. were reported as inactive. Those that were reported as active were tested at the $ID_{50}$ dose against 400 μg per ml. of arachidonic acid. Compounds which did not inhibit arachidonic acid-induced aggregation are reported as potentional phospholiphase $A_2$ inhibitors. The data is tabulated in Table IV. The compounds are shown to inhibit phospholipase $A_2$ from humans at low dosages.

EXAMPLE 3

Some of the compounds of this invention were tested in vivo for their ability to inhibit the effects of UV induced erythema on the skin of guinea pigs. This is an example of an inflammatory process fulfilling the four pathological requirements of "rubor, calor, dolor, and tumor" i.e., reddening, heat, pain, and edematious swelling in the skin. Administration of the compounds of this invention to guinea pigs whose skin was subsequently exposed to ultraviolet light markedly retarded and in some cases eliminated altogether this inflammatory process. Administration of the compounds of this invention was performed both interparenterally and subcutaneously with equivalent results, thereby eliminating any possiblity of reduction in erthyma due to the so called "counter irritant" effect on the serosal soft surface of the gut.

The test was carried out as follows: Guinea pigs of the Hartley strain ranging in weight from 250 to 750 gm. were clipped with coarse and fine clippers to remove as much hair as possible from the back or abdomen. They were then treated with a commercial depilatory for six to seven min. after which they were washed with warm water. The animals were then injected I.P. or subcutaneously with solutions or suspensions of the test compounds made up at 0.02 molar concentrations. The dose was 0.3 ml. per 100 gm. of body weight. A control (untreated) group was also maintained. The animals were then held for 30 min. before being exposed as rapidly as possible to ultra-violet light using a Kromayer lamp for 30 sec. A scoring system was developed to quantitate the erythema. The scoring was from 0 to 5 and is described as follows:

0 = no apparent reddening of the skin
0.5 = some slight reddening, without a definite border
1.0 = a discrete pink circle with a definite border
2.0 = a discrete circle of redness with a definite border more intense than 1.0
3.0 = same circle with still greater intensity
4.0 = same circle with a near maximal response but without any raising of the erythematous spot above the level of the surrounding skin
5.0 = a raised edematous circle with the redness at maximal intensity The animals were scored at hourly intervals for the first four hours. The erythema reached a maximum at this time in the control animals. The major difference between results at 4 hr. and those at 24 is the developement of edema and this occurred in some of the animals treated with phospholipase inhibitors without erythema being present. The results of this test are shown in tabular form in Tables VI and VII. The aggregate scores of the animals treated with the designated compounds are recorded at hourly intervals and compared with the control (untreated) scores. As shown by the tables, the method of this invention markedly retarded UV-induced erythema.

The above tests are illustrative of the advantageous effects of the novel method of this invention. The ability of these compounds as phospholipase $A_2$ inhibitors, both in vitro and in vivo, is demonstrated by the experimental results reported above. They are merely illustrative as to the operation of the method and certainly not limiting as to the possible applications of this invention.

TABLE I

| HOG PANCREAS PHOSPHOLIPASE $A_2$ | |
|---|---|
| COMPOUND[1] | $I_{50}$ Molarity ($\times 10^{-5}$) |
| A | 0.51 |
| B | 1.07 |
| C | 1.18 |
| D | 1.49 |
| E | 2.98 |
| F | 4.37 |
| G | 5.53 |
| I | 2.43 |

$I_{50}$ = concentration of compound for 50% inhibition of phospholipase $A_2$
[1]See Table V for compound name and structure.

TABLE II

| SNAKE VENOM PHOSPHOLIPASE $A_2$ | |
|---|---|
| COMPOUND[1] | $I_{50}$ Molarity ($\times 10^{-4}$) |
| C | 3.01 |
| I | 2.21 |

$I_{50}$ = concentration of compound for 50% inhibition of phospholipase $A_2$
[1]See Table V for compound name and structure.

TABLE III

| BEE VENOM PHOSPHOLIPASE $A_2$ | |
|---|---|
| COMPOUND[1] | $I_{50}$ Molarity ($\times 10^{-4}$) |
| C | 4.04 |

$I_{50}$ = concentration of compound for 50% inhibition of phospholipase $A_2$
[1]See Table V for compound name and structure.

TABLE IV

| HUMAN PLATELET PHOSPHOLIPASE $A_2$ | |
|---|---|
| COMPOUND[1] | $I_{50}$ μg/ml collagen |
| B | 70 |
| C | 75 |
| D | 100 |
| F | 25 |
| G | 30 |

$I_{50}$ = concentration of compound for 50% of phospholipase $A_2$
[1]See Table V for compound name and structure.

TABLE V
KEY

| COMPOUND | NAME | STRUCTURE |
|---|---|---|
| A | Butyrophenone, 4'-fluoro-4-[[4-(α,α,α-trifluoro-p-tolyl)-cyclohexyl]amino]-, trans-, hydrochloride | $F_3C$—⟨⟩—⟨⟩—NH—$CH_2CH_2CH_2$—C(=O)—⟨⟩—F . HCl |
| B | Butyrophenone, 4'-fluoro-4-[(c-4-methoxy-4-o-tolylcyclohexyl)-amino]-, hydrochloride, hemihydrate | $CH_3O$, o-tolyl cyclohexyl structure, NH—$CH_2CH_2CH_2$—C(=O)—⟨⟩—F . HCl . ½ $H_2O$ |
| C | Butyrophenone, 4'-fluoro-4-[(t-4-methoxy-4-o-tolylcyclohexyl)-amino]-, hydrochloride | $H_3C$, $CH_3O$, cyclohexyl, NH—$CH_2CH_2CH_2$—C(=O)—⟨⟩—F . HCl |
| D | Butyrophenone, 4'-fluoro-4-[(c-4-methoxy-4-p-tolyl-r-1-cyclohexyl)amino]-, hydrochloride | $CH_3O$, cyclohexyl, p-tolyl ($CH_3$), NH—$CH_2CH_2CH_2$—C(=O)—⟨⟩—F . HCl |
| E | Butyrophenone, 4'-chloro-4-[[c-4-(hydroxymethyl)-4-phenyl-r-1-cyclohexyl]amino]-, hydrochloride | HO—$CH_2$, cyclohexyl, phenyl, NH—$CH_2CH_2CH_2$—C(=O)—⟨⟩—Cl . HCl |
| F | Butyrophenone, 4'-fluoro-4-[[c-4-(hydroxymethyl)-t-4-phenyl-r-1-cyclohexyl]methylamino]- | HO—$CH_2$, cyclohexyl, phenyl, $CH_3$-N—$CH_2CH_2CH_2$—C(=O)—⟨⟩—F |
| G | Butyrophenone, 4-[[t-4-(p-chlorophenyl)-c-4-(hydroxymethyl)-r-1-cyclohexyl]amino]-4'fluoro-, hydrochloride | Cl—⟨⟩, HO—$CH_3$, cyclohexyl, NH—$CH_2CH_2CH_2$—C(=O)—⟨⟩—F . HCl |
| H | Butyrophenone, 4[[4-(p-chlorophenyl)cyclohexyl]-amino]-4'-fluoro-, hydrochloride | Cl—⟨⟩—⟨⟩—NH—$CH_2CH_2CH_2$—C(=O)—⟨⟩—F . HCl |
| I | Butyropehnone, 4'-fluoro-4-[[4-(hydroxymethyl)-4-phenylcyclohexyl]amino]-cis-, hydrochloride | HO—$CH_2$, cyclohexyl, phenyl, NH—$CH_2CH_2CH_2$—C(=O)—⟨⟩—F . HCl |

TABLE VI
GUINEA PIG ERYTHEMA SCORES[1] INTRAPERITONEAL ADMINISTRATION

| Compound | I | II | III | IV | V | VI | VII | VIII |
|---|---|---|---|---|---|---|---|---|
| B | 25.2 mg/kg | 3 | 5 | 5 | 2 | 15 | 36 | 51 |
| C | 25.2 mg/kg | 8 | 13 | 12 | 12 | 45 | 27 | 72 |
| F | 23 mg/kg | 14 | 12 | 12 | 17 | 55 | 60 | 105 |
| [2]Control | — | 12 | 18 | 24 | 30 | 78 | 50 | 128 |

I - mg/kg Administered
II - 1 hour
III - 2 hours
IV - 3 hours
V - 4 hours
VI - (After 4 hours) Total Points
VII - 24 hours
VIII - (After 24 hours) Total Points
[1]Aggregate scores for 3 animals.
[2]Average aggregate score of 4 runs of 3 animals each. Animals injected with sterile vehicle only.

TABLE VII

GUINEA PIG ERYTHEMA SCORES[1]
SUBCUTANEOUS ADMINISTRATION

| Compound | I | II | III | IV | V | VI | VII | VIII |
|---|---|---|---|---|---|---|---|---|
| B | 64.3 mg/kg | 8 | 7 | 6 | 13 | 34 | 33 | 66 |
| C | 62.99 mg/kg | 10 | 11 | 9 | 10 | 39 | 40 | 79 |
| G | 66.1 mg/kg | 12 | 13 | 9 | 13 | 46 | 52 | 98 |
| H | 61.6 mg/kg | 6 | 6 | 7 | 9 | 28 | 52 | 78 |
| I | 60.9 mg/kg | 2 | 4 | 6 | 7 | 18 | 40 | 58 |
| [3]Control | — | 17 | 23 | 29 | 34 | 103 | 56 | 158 |

I - mg/kg[2] Administered
II - 1 hour
III - 2 hours
IV - 3 hours
V - 4 hours
VI - (After 4 hours) Total Points
VII - 24 hours
VIII - (After 24 hours) Total Points

[1]Aggregate scores for 3 animals.
[2]Higher dosages are to compensate for the much greater absorption by the I.P. route.
[3]Average aggregate score of 3 runs of 3 animals each. Animals injected with sterile vehicle only.

CHART A
BUTYROPHENONE PREPARATION

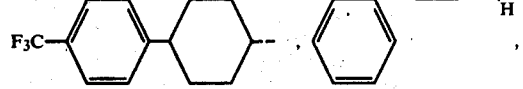

IV                V

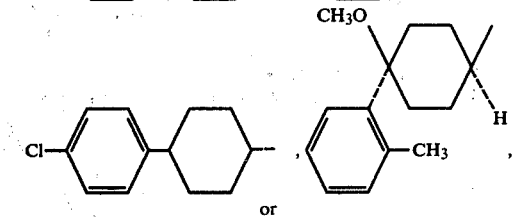

VI

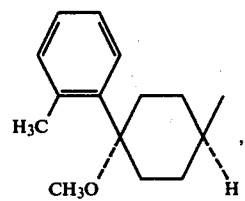

VII

Ar = $C_6H_5$, p-$C_6H_4OCH_3$ or similar substituents to obtain the desired compound.

I claim:

1. A method for treating a phospholipase $A_2$ mediated condition (PMC) in a mammal suffering from the development of said PMC which comprises administering to said mammal an amount of a compound of formula I:
wherein $R_1$ is $R_1$—N($R_3$)—$CH_2$—$CH_2$—$CH_2$—$R_2$

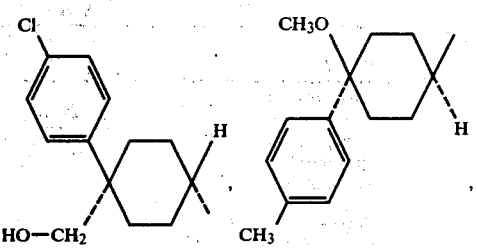

$R_2$ is

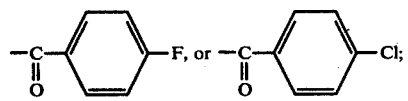

$R_3$ is H or $CH_3$, with the proviso that $R_3$ is -$CH_3$ only when $R_1$ is

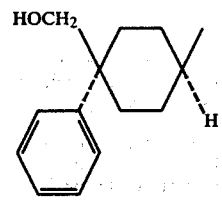

or a pharmacologically acceptable acid addition salt or salt hydrate thereof, effective to treat said PMC.

* * * * *

UNITED STATES PATENT OFFICE
CERTIFICATE OF CORRECTION

Patent No. 4,239,780            Dated  16 December 1980

Inventor(s)   Donald P. Wallach

It is certified that error appears in the above-identified patent and that said Letters Patent are hereby corrected as shown below:

Face Page, in the Abstract, should read -- Phospholipase $A_2$ Inhibition -- as a title and a new paragraph -- The present invention ... --.
Column 10, line 4, the formula should appear as follows instead of as in the patent

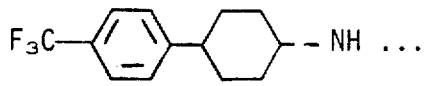

Column 9, Compound I, "Butyropehnone-" should read -- Butyrophenone- --.
Column 11, line 57, "wherein $R_1$ is $R_1-N(R_3)-CH_2-CH_2-CH_2-R_2$" should read -- $R_1-N(R_3)-CH_2-CH_2-CH_2-R_2$ wherein $R_1$ is --.

Signed and Sealed this

Eighth Day of September 1981

[SEAL]

Attest:

Attesting Officer

GERALD J. MOSSINGHOFF

Commissioner of Patents and Trademarks